United States Patent [19]

Takaya et al.

[11] 4,370,326

[45] Jan. 25, 1983

[54] CEPHEM COMPOUNDS AND COMPOSITION

[75] Inventors: Takao Takaya, Sakai; Zenzaburo Tozuka, Toyonaka, both of Japan

[73] Assignee: Fujisawa Pharmaceutical Co., Ltd., Osaka, Japan

[21] Appl. No.: 939,982

[22] Filed: Sep. 6, 1978

[30] Foreign Application Priority Data

Sep. 13, 1977 [GB] United Kingdom ............... 38163/77
Oct. 11, 1977 [GB] United Kingdom ............... 42315/77

[51] Int. Cl.³ ................. C07D 501/22; A61K 31/545
[52] U.S. Cl. ..................................... 424/246; 544/22; 544/16
[58] Field of Search ............ 544/28, 30, 27, 16, 544/22, 26; 424/246

[56] References Cited

U.S. PATENT DOCUMENTS

| | | | |
|---|---|---|---|
| 3,989,695 | 11/1976 | Scartazzini et al. | 544/16 |
| 4,098,888 | 7/1978 | Ochiai et al. | 544/21 |
| 4,147,864 | 4/1979 | Woodward et al. | 424/246 |
| 4,152,432 | 5/1979 | Keymes et al. | 544/22 |
| 4,152,433 | 5/1979 | Kamiya et al. | 424/246 |
| 4,166,115 | 8/1979 | Takaya et al. | 424/246 |
| 4,191,762 | 3/1980 | Kamiya et al. | 424/246 |
| 4,269,977 | 5/1981 | Peter et al. | 544/16 |
| 4,303,655 | 12/1981 | Kamiya et al. | 424/246 |
| 4,342,760 | 8/1982 | Hashimoto et al. | 544/16 |

FOREIGN PATENT DOCUMENTS

| | | |
|---|---|---|
| 2805655 | 8/1978 | Fed. Rep. of Germany . |
| 2710902 | 9/1978 | Fed. Rep. of Germany . |
| 51-149296 | 12/1976 | Japan . |
| 53-112985 | 6/1978 | Japan . |

OTHER PUBLICATIONS

CA. vol. 87(1977) 53334r.
CA. vol. 90(1979) 38941d.

*Primary Examiner*—Nicholas S. Rizzo
*Attorney, Agent, or Firm*—Oblon, Fisher, Spivak, McClelland & Maier

[57] ABSTRACT

This invention relates to novel cephem compounds of high antimicrobial activity of the formula:

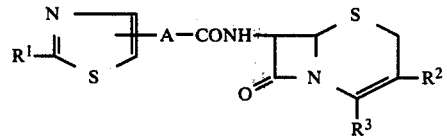

wherein
$R^1$ is amino or protected amino,
A is lower alkylene which may be substituted with oxo, hydroxy, amino, protected hydroxy or protected amino,
$R^2$ is hydrogen, halogen or hydroxy, and
$R^3$ is carboxy or functionally modified carboxy, its non-toxic, pharmaceutically acceptable salt and a bioprecursor thereof.

13 Claims, No Drawings

CEPHEM COMPOUNDS AND COMPOSITION

This invention relates to new cephem compound. More particularly, it relates to new 7-substituted-3-cephem-4-carboxylic acid, its pharmaceutically acceptable salt and pharmaceutically acceptable bioprecursor thereof, which have antimicrobial activities and are also useful as intermediates for preparing other highly potent antimicrobial cephem compounds, and processes for preparation thereof, and to pharmaceutical composition comprising the same and methods of using the same prophylactically and therapeutically for treatment of infectious diseases in human being and animals.

Accordingly, the objects of this invention are to provide:

new 7-substituted-3-cephem-4-carboxylic acid, its pharmaceutically acceptable salt and pharmaceutically acceptable bioprecursor thereof, which exhibit excellent antimicrobial activities against a wide variety of pathogenic microorganisms including Gram negative and Gram positive bacteria, processes for preparation of the same, pharmaceutical composition comprising one of the same as an active ingredient, and a method of using the same prophylactically and therapeutically for treatment of infectious diseases caused by pathogenic microorganisms in human being and animals.

The cephem compounds provided by this invention include the ones represented by the formula (I):

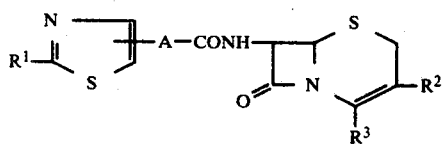

wherein
$R^1$ is amino or protected amino,
A is lower alkylene which may be substituted with oxo, hydroxy, amino, protected hydroxy or protected amino,
$R^2$ is hydrogen, halogen or hydroxy, and
$R^3$ is carboxy or functionally modified carboxy,
and pharmaceutically acceptable salts and bioprecursors thereof.

It is to be noted that the cephem compounds (I) as illustrated above include a compound useful as an antimicrobial agent and also a compound useful as an intermediate for preparing the other antimicrobial agent, particularly as illustrated below.

The terms and definitions described in this specification are illustrated as follows.

As being well known, the 2-amino- or 2-protected amino-thiazolyl group lies in tautomeric relation with the corresponding 2-imino- or 2-protected iminothiazolinyl group. The tautomerism between the said thiazolyl and thiazolinyl groups can be illustrated by the following equilibrium:

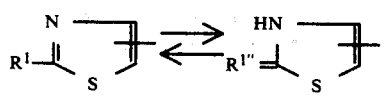

wherein $R^1$ is amino or protected amino, and
$R^{1'}$ is imino or protected imino.

Accordingly, it is to be understood that both of the said groups are substantially the same, and the tautomers consisting of such groups are regarded as the same compounds, especially in the manufacturing chemistry. Therefore, both of the tautomeric forms of the compounds having such groups in their molecule are included in the scope of this invention and designated inclusively with one expression "2-amino- or protected amino-thiazolyl" and represented by the formula:

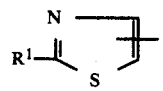

(wherein $R^1$ is as defined above) for the convenient sake throughout this specification.

And further, it is well known that the 3-hydroxy-3-cephem compound having the partial structure of the formula:

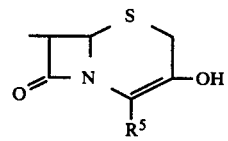

lies in a tautomeric relation with the 3-oxo-cephem compound of the formula:

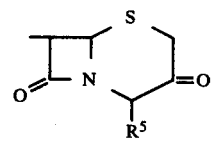

each of which is referred to as the enol- or ketotautomer, and that the enol-tautomer is usually the stabilized one.

Accordingly, both of the compounds having such tautomeric structures are included within the same scope of the compound, and therefore, the structure and nomenclature of such tautomers are expressed inclusively with one expression of the stabilized enol tautomer, i.e. "3-hydroxy-3-cephem" compound, throughout this specification.

In the above and subsequent descriptions of this specification, suitable examples and illustration of the various definitions which this invention intends to include within the scope thereof are explained in detail as follows.

"Lower alkylene" for A may be straight or branched bivalent hydrocarbon residue such as methylene, ethylene, trimethylene, propylene, ethylethylene, tetramethylene, pentamethylene, 1-methylpentamethylene, 2-methylpentamethylene, 3-methylpentamethylene, hexamethylene and the like and more preferable one may be alkylene of 1 to 4 carbon atoms and the most preferable one is methylene.

"Lower alkylene substituted with oxo" for A may be referred to as "oxo(lower)alkylene", and particularly it may be oxomethylene, oxoethylene, 1-oxotrimethylene, 2-oxotrimethylene, 2-oxotetramethylene, 3-oxopentamethylene, and the like, and more preferably the one having 1 to 4 carbon atoms and the most preferably oxomethylene (namely, carbonyl).

"Lower alkylene substituted with hydroxy" for A may be referred to as "hydroxy(lower)alkylene", and particularly it may be hydroxymethylene, hydroxyethylene, 1-hydroxytrimethylene, 2-hydroxytrimethylene, 2-hydroxytetramethylene, 3-hydroxypentamethylene, and the like, more preferably the one having 1 to 4 carbon atoms and the most preferably hydroxymethylene.

"Lower alkylene substituted with amino" for A may be referred to as "amino(lower)alkylene", and particularly it may be aminomethylene, aminoethylene, 1-aminotrimethylene, 2-aminotrimethylene, 1-amino-3-methyltrimethylene, 2-aminotrimethylene, 3-aminopentamethylene and the like, more preferably the one having 1 to 4 carbon atoms and the most preferably aminomethylene.

Suitable "protected hydroxy" group in the definition for A may include an acyloxy and hydroxy substituted with a conventional protective group other than the acyl group (e.g. benzyl, tetrahydropyranyl, etc.). And, suitable acyl moiety in the "acyloxy" as mentioned above can be referred to the same examples of "acyl" as illustrated hereinafter for that of "acylamino" for $R^1$, and preferable examples of "acyloxy" may be substituted or unsubstituted lower alkanoyloxy, substituted or unsubstituted lower alkoxycarbonyloxy, substituted or unsubstituted ar(lower)alkanoyloxy, heterocycle(lower)alkanoyloxy and the like.

Suitable "protected amino" group in the definition for A includes the same ones as the "protected amino" for $R^1$ as illustrated in the following.

"Protective group" in the "protected amino" for $R^1$ may be the conventional N-protective group such as substituted or unsubstituted ar(lower)alkyl (e.g. benzyl, benzhydryl, trityl, 4-methoxybenzyl, 3,4-dimethoxybenzyl, etc.), halo(lower)alkyl (e.g. trichloromethyl, trichloroethyl, trifluoromethyl, etc.), tetrahydropyranyl, substituted phenylthio, substituted alkylidene, substituted aralkylidene, substituted cycloalkylidene, acyl, or the like.

Suitable acyl for the protective group may be substituted or unsubstituted lower alkanoyl (e.g. formyl, acetyl, chloroacetyl, trifluoroacetyl, etc.), substituted or unsubstituted ar(lower)alkanoyl (e.g. phenylacetyl, phenylpropionyl, etc.), substituted or unsubstituted lower alkoxycarbonyl (e.g. methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, trichloroethoxycarbonyl, 2-pyridylmethoxycarbonyl, etc.), substituted or unsubstituted ar(lower)alkoxycarbonyl (e.g. benzyloxycarbonyl, benzhydryloxycarbonyl, 4-nitrobenzyloxycarbonyl, etc.), lower cycloalkoxycarbonyl (e.g. cyclopentyloxycarbonyl, cyclohexyloxycarbonyl, etc.), 8-quinolyloxycarbonyl, succinyl, phthaloyl, or the like.

And further, the reaction product of a silan-, boron-, aluminium- or phosphorus-compound with the amino group may also be included in the protective group. Suitable examples of such compounds may be trimethylsilyl chloride, trimethoxysilyl chloride, boron trichloride, butoxyboron dichloride, aluminum trichloride, diethoxy aluminum chloride, phosphorus dibromide, phenylphosphorus dibromide, or the like.

"Halogen" for $R^2$ may be chlorine, bromine, iodine or fluorine, and preferred one is chlorine or bromine.

"Functionally modified carboxy" for $R^3$ may be an ester amide or the like, and preferably an ester.

Suitable examples of the ester may be alkyl ester (e.g. methyl ester, ethyl ester, propyl ester, isopropyl ester, butyl ester, isobutyl ester, t-butyl ester, pentyl ester, t-pentyl ester, hexyl ester, heptyl ester, octyl ester, 1-cyclopropylethyl ester, etc.); alkenyl ester (e.g. vinyl ester, allyl ester, etc.); alkynyl ester (e.g. ethynyl ester, propynyl ester, etc.); alkoxyalkyl ester (e.g. methoxymethyl ester, ethoxymethyl ester, isopropoxymethyl ester, 1-methoxyethyl ester, 1-ethoxyethyl ester, etc.); alkylthioalkyl ester (e.g. methylthiomethyl ester, ethylthiomethyl ester, ethylthioethyl ester, isopropylthiomethyl ester, etc.); haloalkyl ester (e.g. 2-iodoethyl ester, 2,2,2-trichloroethyl ester, etc.); alkanoyloxyalkyl ester (e.g. acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, palmitoyloxymethyl ester, etc.); alkanesulfonylalkyl ester (e.g. mesylmethyl ester, 2-mesylethyl ester, etc.); substituted or unsubstituted aralkyl ester (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); substituted or unsubstituted aryl ester (e.g. phenyl ester, tolyl ester, t-butylphenyl ester, xylyl ester, mesityl ester, cumenyl ester, salicyl ester, etc.); an ester with a silyl compound such as trialkylsilyl compound, dialkylalkoxysilyl compound or trialkoxysilyl compound, for example, trialkylsilyl ester (e.g. trimethylsilyl ester, triethylsilyl ester, etc.), dialkylalkoxysilyl ester (e.g. dimethylmethoxysilyl ester, dimethylethoxysilyl ester, diethylmethoxysilyl ester, etc.) or trialkoxysilyl ester (e.g. trimethoxysilyl ester, triethoxysilyl ester, etc.) or the like.

With regard to the terms "protected hydroxy", "protected amino" and "functionally modified carboxy" in the above, it is to be understood that these groups bear the meaning not only in synthetic manufacture of the object compound by chemical process(es), but also in physiological and pharmaceutical properties of the object compound per se. That is, in the meaning of the synthetic manufacture, free hydroxy group, free amino group and/or free carboxy group may be transformed into the "protected hydroxy", "protected amino" and/or "functionally modified carboxy" as mentioned above before conducting the process(es) for preventing any possible undesired side reaction(s), and the "protected hydroxy", "protected amino" and/or "functionally modified carboxy" group in the resultant compound may be transformed into free hydroxy, amino and/or carboxy group after the reaction is conducted. This will be apparent from the explanation of the processes in the following.

On the other hand, in the meaning of the physiological and pharmaceutical properties of the object compound, the compound bearing the "protected hydroxy", "protected amino" and/or "functionally modified carboxy" group is optionally used for improving the properties such as solubility, stability, absorbability, toxicity of the particularly active object compound bearing the free hydroxy, free amino and/or carboxy group.

Suitable "pharmaceutically acceptable salt" of the object compound (I) may be conventional non-toxic salt, and may include a salt with an inorganic base or acid, for example, a metal salt such as an alkali metal salt (e.g. sodium salt, potassium salt, etc.) and an alkaline earth metal salt (e.g. calcium salt, magnesium salt, etc.), ammonium salt, an inorganic acid salt (e.g. hydrochloride, hydrobromide, sulfate, phosphate, carbonate, bicarbonate, etc.), a salt with an organic base or acid, for example, an amine salt (e.g. trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt, phenethylbenzylamine salt, etc.), an organic carboxylic or sulfonic acid salt (e.g. acetate, maleate, lactate, tartrate, mesylate, benzenesulfonate, tosylate, etc.), a basic or acidic amino acid salt (e.g. arginine salt, aspartic acid salt, glutamic acid salt, lysine salt, serine salt, etc.) and the like.

It is well known in the pharmaceutical field that the active drug, when it has any undesired physiological and/or pharmaceutical property such as solubility, stability, absorbability, etc. is converted into modified derivative thereof for improving such undesired properties, and then said derivative, upon administration to a patient, exhibits the active efficacy by being converted to the parent drug in the body. In this meaning, the term "pharmaceutically acceptable bioprecursor38 used throughout this specification is intended to fundamentally mean all of the modified derivatives, which have structural formulae different from those of the active compounds of this invention, but are converted in the body to the active compounds of this invention upon administration, and also to mean the derivatives which are sometimes derived physiologically from the compounds of this invention in the body and exhibit antimicrobial efficacy.

The compound (I) of this invention can be prepared by processes as shown in the following scheme.

Process A:
N-Acylation

Process B:
Thiazole ring formation

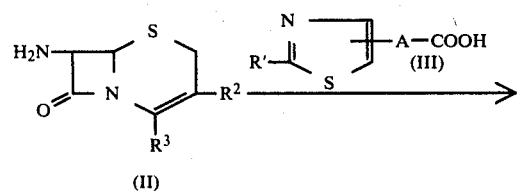

Process C:
Reductive formation of amino(lower)alkylene

Process D:
Reductive formation of hydroxy(lower)alkylene

Process E:
Elimination of amino protective group

Process F:
Carboxy formation

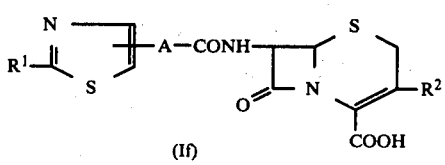

(If)

wherein
$R^1$, $R^2$, $R^3$ and A are each as defined above,
X is halogen,
$R_a^1$ is protected amino,
$R_a^3$ is functionally modified carboxy,
$A^1$ is lower alkylene which may be substituted with hydroxy amino, protected hydroxy or protected amino,
$A^2$ is lower alkylene substituted with a group of the formula: $=N-OR^4$ wherein $R^4$ is hydrogen, lower alkyl, lower alkenyl, lower alkynyl or cycloalkyl,
$A^3$ is amino(lower)alkylene,
$A^4$ is oxo(lower)alkylene, and
$A^5$ is hydroxy(lower)alkylene Process A:
N-Acylation A compound (I) and its salt can be prepared by reacting a 7-amino-3-cephem compound (II), its reactive derivative at the amino or a salt thereof with a carboxylic acid (III), its reactive derivative at the carboxy or a salt thereof according to a conventional manner of so-called N-acylation reaction well known in β-lactam chemistry.

Suitable reactive derivative at the amino group of the compound (II) may include a conventional reactive derivative as used in a wide variety of amidation reaction, for example, isocyanato, isothiocyanato, a derivative formed by the reaction of a compound (II) with a silyl compound (e.g. trimethylsilylacetamide, bis(trimethylsilyl)acetamide, etc.), with an aldehyde compound (e.g. acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc., or the corresponding hydrate, acetal, hemiacetal or enolate thereof), with a ketone, compound (e.g. acetone, methyl ethyl ketone, methyl isobutyl ketone, acetylacetone, ethyl acetoacetate, etc., or the corresponding ketal, hemiketal or enolate thereof), with phosphorus compound (e.g. phosphorus oxychloride, phosphorus chloride, etc.), or with a sulfur compound (e.g. thionyl chloride, etc.) and the like.

Suitable salt of the compound (II) may be referred to the one as exemplified for the compound (I).

Suitable reactive derivative at the carboxy group of the compound (III) may include, for example, an acid halide, an acid anhydride, an activated amide, an activated ester, and the like, and preferably acid halide such as acid chloride or acid bromide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorus acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.); a symmetrical acid anhydride; an activated acid amide with imidazole, 4-substituted imidazole, dimethylpyrazole, triazole or tetrazole; an activated ester (e.g. cyanomethyl ester, methoxymethyl ester, dimethylaminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

Suitable salt of the compound (III) may include a salt with an inorganic base such as alkali metal salt (e.g. sodium salt, potassium salt, etc.) and an alkaline earth metal salt (e.g. calcium salt, magnesium salt, etc.), a salt with an organic base such as tertiary amine salt (e.g. trimethylamine salt, triethylamine salt, N,N-dimethylaniline salt, pyridine salt, etc.), a salt with an inorganic acid (e.g. hydrochloride, hydrobromide, etc.) and the like.

The suitable reactive derivatives of the compounds (II) and (III) can optionally be selected from the above according to the kind of the compounds (II) and (III) to be used practically, and to the reaction conditions.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other solvent which does not adversely influence the reaction, or an optional mixture thereof.

When the acylating agent (III) is used in a form of free acid or salt in this reaction, the reaction is preferably carried out in the presence of a condensing agent such as a carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a bisimidazolide compound (e.g. N,N'-carbonylbis(2-methylimidazole), etc.), an imine compound (e.g. pentamethyleneketene-N-cyclohexylimine, diphenylketene-N-cyclohexylimine, etc.), an olefinic or acetylenic ether compound (e.g. ethoxyacetylene, β-chlorovinylethyl ether, etc.), 1-(4-chlorobenzenesulfonyloxy)-6-chloro-1H-benzotriazole, N-ethylbenzisoxazolium salt, N-ethyl-5-phenylisoxazolium-3'-sulfonate, a phosphorus compound (e.g. polyphosphoric acid, trialkyl phosphite, ethyl polyphosphate, isopropyl polyphosphate, phosphorus oxychloride, phosphorus trichloride, diethylchlorophosphite, orthophenylene chlorophosphite, etc.), thionyl chloride, oxalyl chloride, Vilsmeier reagent prepared by the reaction of dimethylformamide with a halogen compound such as thionyl chloride, phosphorus oxychloride, phosgene or the like.

The protective group in the protected amino, and protected hydroxy group of the compound (III) and the functionally modified carboxy group of the compound (II) may occasionally be transformed into free amino, hydroxy and carboxy group respectively in the course of the reaction or post-treatment in this process, and these cases are included within the scope of this invention.

The object compound (I) and salt thereof are useful as an antimicrobial agent, and a part thereof can also be used as a starting material in the following processes.

Process B:

Thiazole ring formation

The starting compound (IV) and its salt to be used in this process can be prepared by reacting a compound (II), its reactive derivative at the amino group or a salt thereof with a compound (III'), its reactive derivative at the carboxy group or reaction equivalent thereof, as illustrated in the following scheme.

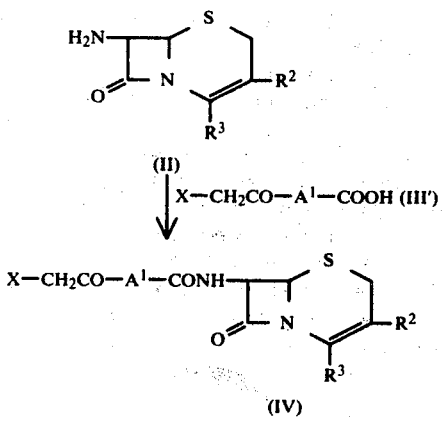

wherein $R^2$, $R^3$ and X are each as defined above.

Suitable "halogen" for X may be chlorine, bromine, iodine, and suitable reactive equivalent of the compound (III') may be a combination of diketene and halogen such as chlorine or bromine. The reaction of a compound (II) with a compound (III') can be conducted substantially in the same manner as the above Process A.

A compound (Ib) and its salt can be prepared by reacting a compound (IV) or its salt with a thiourea compound (V).

The reaction is usually conducted in a solvent such as water, alcohol (e.g. methanol, ethanol, etc.), benzene, dimethylformamide, tetrahydrofuran or any other solvent which does not adversely influence the reaction, within a temperature range of an ambient temperature to heating.

Process C:

Reductive formation of amino(lower)alkylene

A compound (Ic) and its salt can be prepared by reducing a compound (VI) or its salt, which can be prepared by reacting a compound (II), its reactive derivative at the amino group or a salt thereof with a compound of the formula:

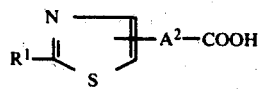

wherein $R^1$ and $A^2$ are each as defined above, its reactive derivative at the carboxy group or a salt thereof, in the same manner as the above Process A.

The reduction in this process may be conducted by a conventional method, for example, catalytic reduction using a conventional catalyst (e.g. Raney nickel, platinum oxide, palladium on carbon, ruthenium on carbon, rhodium on alumina, copper chromium oxide, etc.); chemical reduction using a combination of an acid (e.g. hydrochloric acid, sulfuric acid, formic acid, acetic acid, etc.) and a metal or a metal salt (e.g. iron, zinc, tin, chromium chloride, chromium acetate, etc.), a combination of a metal or an amalgam (e.g. sodium, zinc amalgam, sodium amalgam, aluminum amalgam, etc.) and a solvent (e.g. water, methanol, ethanol, etc.), or a reducing agent such as a complex of metal hydride (e.g. sodium borohydride, alkyl-tin-hydride, lithium aluminum hydride, diethyl aluminum hydride, etc.); electrolytic reduction or the like. The reaction conditions such as temperature, pressure, time and solvent can be selected according to the kinds of the starting compound (VI) and the reduction method to be applied.

Process D:

Reductive formation of hydroxy(lower)alkylene

A compound (Id) and its salt can be prepared by reducing a compound (Id') or its salt, which can be prepared by the above Process A.

The reduction method of this process may be a conventional one which can be applied for the reduction of oxo group into hydroxy group, and particular of which is substantially the same as those explained in the above Process C.

Process E:

Elimination of amino-protective group

A compound (Ie) and its salt can be prepared by subjecting a compound (Ie') or its salt to elimination reaction of the amino-protective group in the protected amino group for $R_a^1$.

The starting compound (Ie') can be prepared, for example, by the above Process A.

The elimination reaction may be conducted in accordance with a conventional method such as hydrolysis, reduction (reductive elimination) or the like. These methods may be selected according to the kind of the amino-protective group to be eliminated.

The hydrolysis may include a method using an acid (acidic hydrolysis), a base (basic hydrolysis) or hydrazine, and the like.

Among these methods, hydrolysis using an acid is one of the common and preferable methods for eliminating the amino-protective group such as an acyl group, for example, substituted or unsubstituted lower alkanoyl, substituted or unsubstituted lower alkoxycarbonyl, substituted or unsubstituted ar(lower)alkoxycarbonyl, lower cycloalkoxycarbonyl, substituted phenylthio, substituted alkylidene, substituted aralkylidene, substituted cycloalkylidene or the like. Suitable acid to be used in this acidic hydrolysis may include an organic or inorganic acid such as formic acid, trifluoroacetic acid, benzenesulfonic acid, p-toluenesulfonic acid, hydrochloric acid, cation-exchange resin, and the like. Preferable acid is the one which can easily be separated out from the reaction product by a conventional manner such as neutralization or distillation under reduced pressure, for example, formic acid, trifluoroacetic acid, hydrochloric acid or the like. The acid suitable for the reaction can be selected in consideration of the chemical property of the starting compound and the product as well as the kind of the protective group to be eliminated. The acidic hydrolysis can be conducted in the presence or absence of a solvent. Suitable solvent may be a conventional organic solvent, water or a mixture thereof, which does not adversely influence this reaction. Particularly, when the hydrolysis is conducted with trifluoroacetic acid, the reaction may be accelerated by addition of anisole.

The hydrolysis using a base can be applied for eliminating the protective group such as an acyl group, preferably, for example, haloalkanoyl (e.g. trifluoroacetyl, etc.) and the like. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as alkali metal acetate (e.g. sodium acetate, potassium acetate, etc.), trialkylamine (e.g. trimethylamine, triethylamine, etc.), picoline, N-methylpyrrolidine, N-methylmorpholine, 1,5-diazabicyclo[4,3,0]-5-nonene, 1,4-diazabicyclo[2,2,2]-octane, 1,5-diazabicyclo[5,4,0]-7-undeceneanion-exchange resin or the like. The hydrolysis using a base is often carried out in water or a conventional organic solvent or a mixture thereof.

The hydrolysis using hydrazine can be applied for eliminating the protective group such as dibasic acyl, for example, succinyl, phthaloyl or the like.

The reductive elimination can be applied for eliminating the protective group such as acyl, for example, halo(lower)alkoxycarbonyl (e.g. trichloroethoxycarbonyl, etc.), substituted or unsubstituted ar(lower)alkoxycarbonyl (e.g. benzyloxycarbonyl, p-nitrobenzyloxycarbonyl, etc.), 2-pyridylmethoxycarbonyl, etc., aralkyl (e.g. benzyl, benzhydryl, trityl, etc.) and the like. Suitable reduction may include, for example, reduction using an alkali metal borohydride (e.g. sodium borohydride, etc.), conventional catalytic hydrogenolysis and the like.

And further, the protective group such as halo(lower)alkoxycarbonyl or 8-quinolyloxycarbonyl can be eliminated by treatment with a heavy metal such as copper, zinc or the like.

The reaction temperature is not critical and may optionally be selected in consideration of the chemical property of the starting compound and reaction product as well as the kind of the N-protective group and the method to be applied, and the reaction is preferably carried out under a mild condition such as under cooling, at ambient temperature or slightly elevated temperature.

The process includes in its scope the cases that the functionally modified carboxy for $R^3$ is simultaneously transformed into the free carboxy group in the course of the above reaction or in the post-treatment.

As to this process, it is to be understood that the purpose of this process lies in providing the generally more active compound (Ie) having an aminothiazolyl group by eliminating the protective group in the protected amino group of the compound (Ie') prepared by the other processes as mentioned above or below.

Process F:

Carboxy formation

This process is to provide a free carboxy compound (If) or its salt, which generally exhibits higher antimicrobial activity as compared with the corresponding functionally modified carboxy compound (If').

Accordingly, the meaning of the functionally modified carboxy in the compound (If') lies in mainly synthetic manufacture by chemical process(es) as illustrated hereinabove.

This process is conducted by transforming the functionally modified carboxy group of the starting compound (If') into free carboxy group, and the preferred functionally modified carboxy for $R_a^3$ in the compound (If') may be an esterified carboxy group as exemplified for $R^3$ of the compound (I).

The method to be applied to this process includes conventional ones such as hydrolysis, reduction and the like.

The method of hydrolysis includes a conventional one using an acid, base, enzyme or enzymatic preparation, and the like.

Suitable examples of the acid and base are to be referred to those as exemplified in the above Process E, and the acidic or basic hydrolysis can be carried out in a similar manner to that of the Process E.

Suitable enzyme includes an esterase and esterase preparation which exhibits an esterase activity such as a cultured broth of microorganism or processed materials of microorganism, the preparation of animal or plant tissues, or the like, and preferably a cultured broth of microoganism or processed material thereof.

An esterase to be used in the enzymatic hydrolysis may be used not only in a purified state, but also in a crude state.

The compound obtained in accordance with the processes as explained above can be isolated and purified in a conventional manner.

In case that the object compound (I) has free carboxy and/or free amino, it may be transformed into its pharmaceutically acceptable salt by a conventional method.

The object compound (I), its pharmaceutically acceptable salt and bioprecursor thereof exhibit high antimicrobial activities inhibiting the growth of a wide variety of pathogenic microorganisms including Gram-positive and Gram-negative bacteria and are useful as antimicrobial agents.

In order to show the utility of the compound (I), the test data of some representative compounds (I) are shown in the following.

In vitro antibacterial activity:

Test Method:

In vitro antibacterial activity was determined by the two-fold agar-plate dilution method as described below.

One loopful of an overnight culture of each test strain in Trypticase-soy broth ($10^8$ viable cells per ml.) was streaked on heart-infusion agar (HI-agar) containing graded concentrations of antibiotics, and the minimal inhibitory concentration (MIC) was expressed in terms of $\mu g/ml$. after incubation at 37° C. for 20 hours.

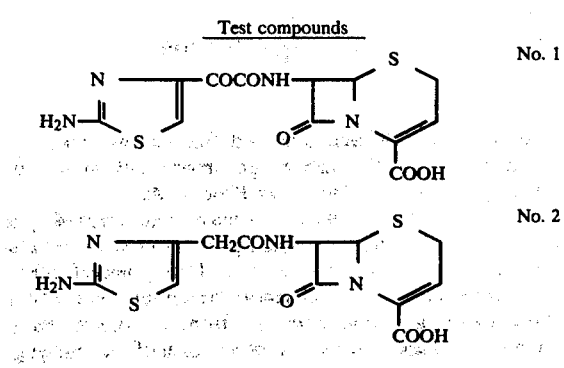

-continued
Test compounds

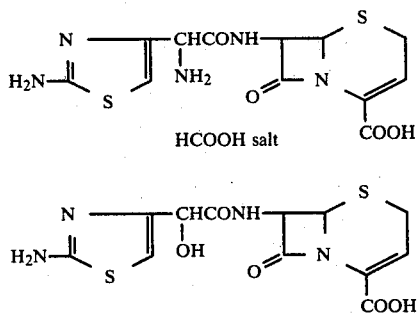

No. 3

No. 4

|  | Test Results MIC (μg/ml) | | | |
| --- | --- | --- | --- | --- |
| Compound No. | 1 | 2 | 3 | 4 |
| Salmonella enteritidis | 1.56 | 1.56 | 3.13 | 3.13 |
| Escherichia coli 324 | 1.56 | 1.56 | 0.78 | 1.56 |
| Klebsiella aerogenes 417 | 0.1 | 0.2 | 0.39 | 0.78 |
| Proteus mirabilis 520 | 0.78 | 0.39 | 0.78 | 1.56 |
| Proteus vulgaris 616 | 12.5 | 6.25 | 1.56 | 12.5 |

For prophylactic and/or therapeutic administration, the active compound (I) of the present invention is used in the form of a conventional pharmaceutical preparation which contains said compound, as an active ingredient, in admixture with pharmaceutically acceptable carriers such as an organic or inorganic solid or liquid excipient which is suitable for oral, parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age and conditions of the patient, a kind of disease and a degree of the infection, and further a kind of the active compound (I) to be applied, etc., an average single dose of about 50 mg., 100 mg., 250 mg. and 500 mg. of the active compound (I) is sufficient for treating infectious diseases caused by pathogenic bacteria. In general, the active compound (I) can be administered in an amount between 1 mg/kg and 100 mg/kg, preferably 5 mg/kg and 50 mg/kg.

And further, it is to be noted that, among the object compound (I), the compound (Id') and its salt are useful as an intermediate for preparing the more active cephalosporin compound of the formula (VI), its nontoxic, pharmaceutically acceptable salt or a bioprecursor thereof.

A compound (VI) and its salt can be prepared by reacting a compound (Id') or its salt with a compound (VII) or its salt as illustrated by the following schema:

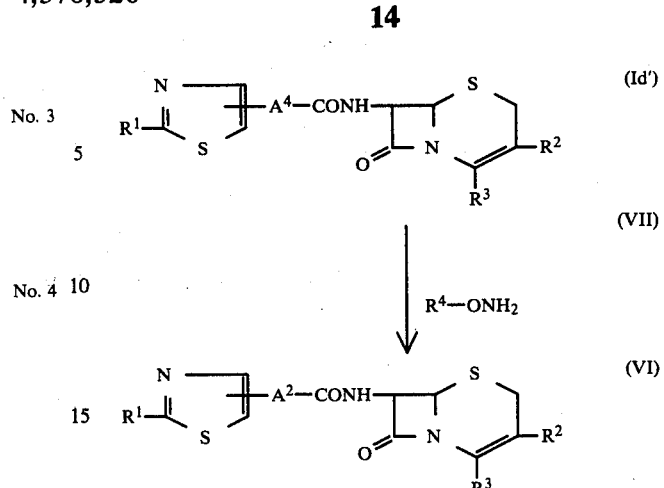

wherein $R^1$, $R^2$, $R^3$, $R^4$, $A^2$ and $A^4$ are each as defined above.

The suitable example of the compound (VII) may be hydroxylamine, lower alkoxyamine (e.g. methoxyamine, ethoxyamine, propoxyamine, butoxyamine, etc.), lower alkenyloxyamine (e.g. vinyloxyamine, allyloxyamine, propenyloxyamine, butenyloxyamine, etc.), lower alkynyloxyamine (e.g. ethynyloxyamine, propynyloxyamine, butynyloxyamine, etc.) or cycloalkoxyamine (e.g. cyclobutoxyamine, cyclopentyloxyamine, cyclohexyloxyamine, etc.).

The salt of the compound (VII) may be acid salt such as hydrochloride, hydrobromide, sulfate or the like.

This reaction is usually conducted in a solvent such as water, alcohol or any other solvent which does not adversely influence the reaction, within a temperature range from cooling to heating.

When a salt of the compound (VII) is used, the reaction is preferably conducted in the presence of a base as exemplified in the Process E.

Still further, it is to be noted that, among the object compounds (I), the compounds (Ic) and (Id) and their salts are also useful as intermediates for preparing the other cephalosporin compounds, which may be prepared by acylating the amino group in the symbol $A^3$ of the compound (Ic) or esterifying the hydroxy group in the symbol $A^5$ of the compound (Id), respectively.

The partial structure of the formula:

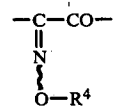

of the compound (VI) is intended to mean both of the geometric formula:

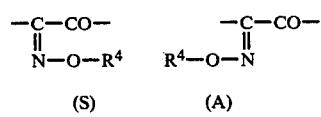

The geometry of the formula (S) is referred to as "syn" and another formula (A) is referred to as "anti". From the view point of structure-activity relationship, it is to be noted that the syn isomer of the compound (VI) tends to be of much higher antimicrobial activity than the corresponding anti isomer, and accordingly the syn isomer of the compound (VI) is more preferable antimicrobial agent than the corresponding anti isomer in the prophylactic and therapeutic value.

Following examples are given only for explaining this invention in more detail.

EXAMPLE 1

(1) 4-Nitrobenzyl 7-amino-3-cephem-4-carboxylate hydrochloride (9 g), trimethylsilylacetamide (24.81 g) and bis(trimethylsilyl)acetamide (9 ml) were added to dry ethyl acetate (100 ml) and stirred at 45° C. for an hour.

On the other hand, phosphoryl chloride (8.4 ml) was added dropwise to a stirred mixture of dimethylformamide (4.0 ml) and dry ethyl acetate (16.0 ml) under ice cooling, and stirred for a while. To the solution were added ethyl acetate (240 ml) and 2-(2-formamido-4-thiazolyl)glyoxylic acid (5.35 g) gradually at −3° C., and the mixture was stirred at the same temperature for 15 minutes. The solution was added dropwise to the solution containing the cephalosporin compound prepared above at −15° C. and stirred at the same temperature for 30 minutes. Water (50 ml) was added to the resultant solution, and the precipitates were collected by filtration, washed with water and dried over phosphorus pentoxide under reduced pressure to give 4-nitrobenzyl 7-[2-formamido-4-thiazolyl)glyoxyloylamino]-3-cephem-4-carboxylate (7.124 g). The ethyl acetate layer was separated from the filtrate, washed with a saturated aqueous solution of sodium chloride, dried over magnesium sulfate, and concentrated under reduced pressure to give the same object compound as above (1.03 g). Total yield 8.154 g.

I.R. $\nu_{max}^{Nujol}$: 1775, 1725, 1650 cm$^{-1}$

N.M.R. $\delta$(DMSO-d$_6$, ppm): 3.66 (2H, m), 5.17 (1H, d, J=5.2 Hz), 5.42 (2H, s), 5.90 (1H, dd, J=5.2 Hz, 7.8 Hz), 6.66 (1H, t, J=5.0 Hz), 7.67 (2H, d, J=9 Hz), 8.22 (2H, d, J=9 Hz), 8.39 (1H, s), 8.55 (1H, s), 9.87 (1H, d, J=7.8 Hz).

(2) A mixture of 4-nitrobenzyl 7-[2-(2-formamido-4-thiazolyl)glyoxyloylamino]-3-cephem-4-carboxylate (3.0 g) methanol (60 ml) and tetrahydrofuran (80 ml) was added to a mixture of 10% palladium-carbon (1.5 g), acetic acid (10 ml) and methanol (10 ml) in an atmosphere of nitrogen gas, and then subjected to catalytic reduction at room temperature under ordinary pressure for 4 hours. The resultant mixture was filtered, and the filtrate was concentrated under reduced pressure. The precipitates were collected by filtration, washed with diisopropyl ether (50 ml) and dried to give powder (1.34 g). A mixture of water (100 ml) and ethyl acetate (100 ml) was added to the powder adjusted to pH 6.0 with sodium bicarbonate and the aqueous layer was separated, washed with ethyl acetate and diethyl ether. The remaining ether was removed off by bubbling with nitrogen gas, and the aqueous solution was adjusted to pH 2.0 with 10% hydrochloric acid. The resultant precipitates were collected by filtration and dried over phosphorus pentoxide to give 7-[2-(2-formamido-4-thiazolyl)glyoxyloylamino]-3-cephem-4-carboxylic acid (0.47 g.) The above filtrate was concentrated under reduced pressure, and the residue was pulverized with a mixture of diethyl ether and petroleum ether. The precipitates were collected by filtration, washed with diethyl ether and petroleum ether and dried under reduced pressure to give the same objective compound (1.1 g). Total yield 1.57 g.

I.R. $\nu_{max}^{Nujol}$: 1780, 1670 cm$^{-1}$

N.M.R. $\delta$(DMSO-d$_6$, ppm): 3.63 (2H, m, J=4 Hz), 5.17 (1H, d, J=5.2 Hz), 5.87 (1H, dd, J=5.2 Hz, 8.2 Hz), 6.53 (1H, t, J=4 Hz), 8.42 (1H, s), 8.59 (1H, s), 9.83 (1H, d, J=8.2 Hz)

(3) A mixture of conc.hydrochloric acid (2.44 g) and methanol (10 ml) was added to a mixture of 7-[2-(2-formamido-4-thiazolyl)glyoxyloylamino]-3-cephem-4-carboxylic acid (2.44 g) in methanol (40 ml) under ice-cooling, stirred at 20° to 22° C. for 5 hours and filtered. The filtrate was concentrated under reduced pressure, and water (100 ml) was added to the residue adjusted to pH 6.5 with sodium bicarbonate with stirring and filtered. The filtrate was washed with ethyl acetate, and adjusted to pH 3.5 with 10% hydrochloric acid. The resultant precipitates were collected by filtration, washed with water and dried over phosphorus pentoxide under reduced pressure to give 7-[2-(2-amino-4-thiazolyl)-glyoxyloylamino]-3-cephem-4-carboxylic acid (0.492 g). The filtrate and washings were subjected to column chromatography on macroporous, non-ionic adsorption resin "Diaion HP-20" (Trademark, manufactured by Mitsubishi Chemical Industries Ltd.), washed with water and eluted with 15% isopropyl alcohol. The isopropyl alcohol was distilled off under reduced pressure and the remaining solution was lyophilized to give the same object compound (1.561 g). Total yield 2.053 g.

I.R. $\nu_{max}^{Nujol}$: 1780, 1668 cm$^{-1}$

N.M.R. $\delta$(D$_2$O, ppm): 3.57 (2H, m), 5.17 (1H, d, J=4.8 Hz), 5.78 (1H,d, J=4.8 Hz), 6.33 (1H, m), 8.26 (1H, s)

EXAMPLE 2

(1) Phosphoryl chloride (0.7 g) was added to N,N-dimethylformamide (10 ml) at 20° C. and stirred at 40° C. for 30 minutes. 2-(2-Formamidothiazol-4-yl)glyoxylic acid (0.4 g) was added to the solution at 0° to 5° C. and stirred for 40 minutes. The solution was added to a solution of 4-nitrobenzyl 7-amino-3-hydroxy-3-cephem-4-carboxylate (0.7 g), trimethylsilylacetamide (1.85 g) and bis(trimethylsilyl)acetamide (1.62 g) in ethyl acetate (20 ml) at −20° C. and stirred at −20° C. for an hour. After adding water (20 ml) to the resultant solution, the ethyl acetate layer was separated, washed with an aqueous solution of sodium bicarbonate, dried over magnesium sulfate and concentrated in vacuo. The residue was triturated with diethyl ether to give 4-nitrobenzyl-7-[2-(2-formamidothiazol-4-yl)glyoxyloylamino]-3-hydroxy-3-cephem-4-carboxylate (0.85 g).

I.R. $\nu_{max}^{Nujol}$: 3150, 1770, 1660, 1600 cm$^{-1}$

N.M.R. $\delta$(DMSO-d$_6$, ppm): 3.58 (2H, AB-q, J=18 Hz), 5.48 (2H, s), 5.25–5.83 (3H, m), 7.75 (2H, d, J=9 Hz), 8.32 (2H, d, J=9 Hz), 8.58 (1H, s), 8.63 (1H, s), 9.92 (1H, t, J=8 Hz)

(2) A mixture of 4-nitrobenzyl 7-[2-(2-formamidothiazol-4-yl)glyoxyloylamino]-3-hydroxy-3-cephem-4-carboxylate (0.7 g) and conc.hydrochloric acid (0.23 g) in methanol (10 ml) was stirred at room temperature for 3 hours. The solvent was evaporated in vacuo and the residue was triturated with diisopropyl ether. The precipitates were collected by filtration and washed with diisopropyl ether to give 4-nitrobenzyl 7-[2-(2-amino-thiazol-4-yl)glyoxyloylamino]-3-hydroxy-3-cephem-4-carboxylate hydrochloride (0.6 g).

I.R. $\nu_{max}^{Nujol}$: 3300, 1770, 1660, 1630, 1600, 1510 cm$^{-1}$

N.M.R. $\delta$(DMSO-d$_6$, ppm): 3.52 (2H, broad s), 5.40 (2H, s), 5.18–5.57 (3H, m), 7.70 (2H, d, J=9 Hz), 8.25 (2H, d, J=9 Hz), 8.27 (1H, s), 9.97 (1H, t, J=9 Hz)

EXAMPLE 3

N,N-Dimethylformamide (88 mg) and phosphorus oxychloride (184 mg) were mixed to prepare Vilsmeier reagent in a conventional manner, and the resultant Vilsmeier reagent was suspended in dry tetrahydrofuran (10 ml). To the suspension was added 2-(2-formamidothiazol-4-yl)glyoxylic acid (0.2 g) under ice-cooling with stirring, and the solution was stirred at the same temperature for 30 minutes to prepare the activated acid solution. 4-Nitrobenzyl 7-amino-3-chloro-3-cephem-4-carboxylate (0.4 g) was dissolved in a solution of trimethylsilylacetamide (1.0 g) in ethyl acetate (100 ml). To the solution was added the activated acid solution obtained above all at once at −20° C., and the solution was stirred at −20° to −5° C. for 1.5 hours. After water and ethyl acetate (50 ml) were added to the resultant solution at −20° C., the insoluble substance was separated by filtration, washed with water and acetone in turn and then dried to give 4-nitrobenzyl 7-[2-(2-formamidothiazol-4-yl)glyoxyloylamino]-3-chloro-3-cephem-4-carboxylate (0.1 g).

I.R. $\nu_{max}^{Nujol}$: 3350, 1780, 1730, 1650, 1600, 1520 cm$^{-1}$

N.M.R. δ(DMSO-d$_6$, ppm): 3.96 (2H, q, J=18 Hz), 5.50 (2H, s), 5.92 (1H, dd, J=5.8 Hz), 7.74 (2H, d, J=9 Hz), 8.28 (2H, d, J=9 Hz), 8.48 (1H, s), 8.60 (1H, s), 10.00 (1H, d, J=8 Hz), 12.63 (1H, broad s)

EXAMPLE 4

(1) 7-Amino-3-cephem-4-carboxylic acid (2.54 g) was dissolved in a solution of trimethylsilylacetamide (11.7 g) and bis(trimethylsilyl)acetamide (15 ml) in dried ethyl acetate (50 ml). A solution of bromine (2.43 g) in dried methylene chloride (10 ml) was added dropwise to a solution of diketene (1.28 g) in dried methylene chloride (25 ml) at −30° C. over 10 minutes and stirred at the same temperature for 1.5 hours. The solution was added to the above solution containing 7-amino-3-cephem-4-carboxylic acid at −15° C. over 10 minutes, and stirred at −15° to −10° C. for 1.5 hours. Water (50 ml) was added to the resultant solution. The ethyl acetate layer was separated, and extracted with aqueous solution of sodium bicarbonate. The aqueous extract was adjusted to pH 2.0 with 10% hydrochloric acid and extracted with ethyl acetate. The ethyl acetate extract was washed with water, dried over magnesium sulfate and concentrated under reduced pressure to give 7-[2-(2-bromoacetyl)acetamido]-3-cephem-4-carboxylic acid (2.82 g).

I.R. $\nu_{max}^{Nujol}$: 1760, 1660 cm$^{-1}$

N.M.R. δ(DMSO-d$_6$, ppm): 3.58 (2H, d, J=4 Hz), 3.65 (2H, s), 4.40 (2H, s), 5.06 (1H, d, J=5 Hz), 5.73 (1H, dd, J=8 Hz, 5 Hz), 6.50 (1H, t, J=4 Hz), 9.08 (1H, d, J=8 Hz)

(2) Thiourea (663 mg), sodium bicarbonate (732 mg) and water (20 ml) were added to a stirred solution of 7-[2-(2-bromoacetyl)acetamido]-3-cephem-4-carboxylic acid (2.11 g) in tetrahydrofuran (20 ml) under ice-cooling and stirred at the same temperature for an hour. After the resultant solution was adjusted to pH 4.0 with dilute hydrochloric acid, the precipitates were collected by filtration, washed with water and dried over phosphorus pentoxide under reduced pressure to give 7-[2-(2-amino-4-thiazolyl)acetamido]-3-cephem-4-carboxylic acid (1.01 g).

I.R. $\nu_{max}^{Nujol}$: 3550, 3330, 1750, 1670, 1620 cm$^{-1}$

N.M.R. δ(DMSO-d$_6$, ppm): 3.42 (2H, s), 3.60 (2H, d, J=4 Hz), 5.08 (1H, d, J=5 Hz), 5.77 (1H, dd, J=8 Hz, 5 Hz), 6.30 (1H, s), 6.52 (1H, t, J=4 Hz), 8.87 (1H, d, J=8 Hz)

EXAMPLE 5

(1) 4-Nitrobenzyl 7-amino-3-cephem-4-carboxylate (5 g) was dissolved in a solution of trimethylsilylacetamide (13.8 g) and bis(trimethylsilyl)acetamide (10 ml) in dry ethyl acetate (50 ml) and stirred at 45° C. for 1.5 hours. A solution of bromine (2.88 g) in methylene chloride (7 ml) was added dropwise to a solution of diketene (1.5 g) in methylene chloride (7 ml) at −40° C. over 20 minutes and stirred at −30° C. for 1 hour. The solution obtained thus was added to dropwise to the above solution of 4-nitrobenzyl 7-amino-3-cephem-4-carboxylate under cooling at −15° C. and then stirred at the same temperature for 30 minutes. Water (50 ml) was added to the resultant solution and extracted with ethyl acetate. The ethyl acetate extract was washed with water, dried over magnesium sulfate and concentrated under reduced pressure to give oily 4-nitrobenzyl 7-[2-(2-bromoacetyl)acetamido]-3-cephem-4-carboxylate (6.15 g).

I.R. $\nu_{max}^{Nujol}$: 1780, 1740, 1630 cm$^{-1}$

N.M.R. δ(DMSO-d$_6$, ppm): 3.62 (2H, broad s), 4.37 (2H, s), 5.08 (1H, d, J=5 Hz), 5.40 (2H, s), 5.77–6.05 (m), 6.67 (1H, t, J=5 Hz), 7.68, 8.04 (4H, m), J=9 Hz), 9.07 (1H, d, J=8 Hz)

(2) Thiourea (1.13 g), sodium bicarbonate (1.24 g) and water (20 ml) were added to a solution of 4-nitrobenzyl 7-[2-(2-bromoacetyl)acetamido]-3-cephem-4-carboxylate (6.15 g) in tetrahydrofuran (60 ml), and stirred at room temperature for an hour. After concentrating the resultant solution under reduced pressure, the residue was extracted with ethyl acetate. The extract was washed with water, dried over magnesium sulfate and concentrated under reduced pressure. The oily residue was subjected to column chromatography on silica gel, and eluted with benzene, a mixture of benzene (1 part) and ethyl acetate (1 part) and then ethyl acetate in turn. The ethyl acetate fractions were collected and concentrated under reduced pressure to give 4-nitrobenzyl 7-[2-(2-amino-4-thiazolyl)acetamido]-3-cephem-4-carboxylate (1.5 g).

I.R. $\nu_{max}^{Nujol}$: 3350, 1780, 1740, 1680, 1610 cm$^{-1}$

N.M.R. δ(DMSO-d$_6$, ppm): 3.40 (2H, broad s), 3.68 (2H, broad s), 5.12 (1H, d, J=5 Hz), 5.43 (2H, s), 5.84 (1H, dd, J=8 Hz, 5 Hz), 6.30 (1H, s), 6.70 (1H, broad s), 7.72 (2H, d, J=9 Hz), 8.27 (2H, d, J=9 Hz), 8.93 (1H, d, J=8 Hz)

(3) A solution of 4-nitrobenzyl 7-[2-(2-amino-4-thiazolyl)acetamido]-3-cephem-4-carboxylate (1.4 g) in a mixture of methanol (25 ml) and tetrahydrofuran (60 ml) was added to a mixture of 10% palladium-on-carbon (1.7 g), glacial acetic acid (7 ml) and methanol (20 ml) in an atmosphere of nitrogen. Hydrogen gas was introduced into the mixture and shaken for 8.5 hours at room temperature. After removing the insoluble substance by filtration, the filtrate was concentrated under reduced pressure. The residue was pulverized with diethyl ether, and the resultant substance was dissolved in an aqueous solution of sodium bicarbonate, washed with ethyl acetate and diethyl ether in turn and then the remaining ether was removed by bubbling with nitrogen gas. The resultant solution was adjusted to pH 4.5 with dilute hydrochloric acid, subjected to column chromatography on macroporous non-ionic adsorption resin "Diaion HP-20" (Trademark, manufactured by Mitsubishi Chemical Industries Ltd.), and eluted with 20% isopropyl alcohol. Isopropyl alcohol was distilled off under reduced pressure and the remaining solution was lyophilized to give 7-[2-(2-amino-4-thiazolyl)acetamido]-3-cephem-4-carboxylic acid (185 mg).

I.R. $\nu_{max}^{Nujol}$: 3550, 3330, 1750, 1670, 1620 cm$^{-1}$

N.M.R. $\delta$(DMSO-d$_6$, ppm): 3.42 (2H, s), 3.60 (2H, d, J=4 Hz), 5.08 (1H, d, J=5 Hz), 5.77 (1H, dd, J=8 Hz, 5 Hz), 6.30 (1H, s), 6.52 (1H, t, J=4 Hz), 8.87 (1H, d, J=8 Hz)

EXAMPLE 6

(1) 7-Amino-3-cephem-4-carboxylic acid (1.7 g) and sodium bicarbonate (2.84 g) were dissolved in a mixture of water (35 ml) and acetone (35 ml). On the other hand, phosphorus oxychloride (1.95 ml) was added dropwise to a suspension of 2-(2-amino-4-thiazolyl)-2-methoxyiminoacetic acid (syn-isomer: 3.42 g) in dry ethyl acetate (34 ml) over 10 minutes at 0° to 6° C., and the mixture was stirred at the same temperature for 30 minutes. To the solution was added dropwise a solution of trimethylsilylacetamide (2.39 g) in ethyl acetate (5 ml) at 0° to 6° C. over 20 minutes, and the mixture was stirred for 20 minutes. After phosphorus oxychloride (1.95 ml) was added dropwise to the mixture at the above temperature over 10 minutes, the mixture obtained thus was stirred for 30 minutes. And further, dimethylformamide (1.29 ml) was added dropwise to the mixture over 10 minutes at the same temperature and stirred for one hour to give a clear solution. The solution was added dropwise to the solution of 7-amino-3-cephem-4-carboxylic acid at −5° to 5° C., over 30 minutes, at pH 6.5 to 7.5, and the reaction mixture was stirred for one hour at the same temperature. Ethyl acetate (200 ml) was added to the resultant solution, and the aqueous layer was separated, washed with methylene chloride, bubbled with nitrogen gas and adjusted to pH 4 with acetic acid. The solution was subjected to column chromatography on macroporous, nonionic adsorption resin "Diaion HP-20" (Trade mark: manufactured by Mitsubishi Chemical Industries Ltd.) and eluted with 20% aqueous solution of isopropyl alcohol. The eluate was concentrated under reduced pressure and lyophilized to give 7-[2-(2-amino-4-thiazolyl)-2-methoxyiminoacetamido]-3-cephem-4-carboxylic acid (syn isomer: 2.0 g)

I.R. $\nu_{max}^{Nujol}$: 3470, 3280, 3200, 1780, 1695 1655, 1622 cm$^{-1}$

N.M.R. $\delta$(DMSO-d$_6$, ppm): 3.60 (2H, broad s), 3.84 (3H, s), 5.12 (1H, dd, J=5 Hz), 5.84 (1H, dd, J=5.8 Hz), 6.52 (1H, broad t), 6.76 (1H, s), 7.26 (2H, broad s), 9.65 (1H, d, J=8 Hz)

(2) Zinc powder (4.5 g) was added to a stirred solution of 7-[2-(2-amino-4-thiazolyl)-2-methoxyiminoacetamido]-3-cephem-4-carboxylic acid (syn isomer: 3 g) in 90% formic acid (150 ml) under ice-cooling over 5 minutes, and stirred at the same temperature for 15 minutes. After the resultant solution was filtered and washed with formic acid, the filtrate and the washings were combined and concentrated under reduced pressure to a volume of about 20 ml. The concentrate was dissolved in water (150 ml) and bubbled with hydrogen sulfide gas for 20 minutes under ice-cooling. The precipitating zinc sulfide was filtered off, and the filtrate was treated with activated charcoal and lyophilized to give 7-[2-(2-amino-4-thiazolyl)glycinamido]-3-cephem-4-carboxylic acid formate (2.9 g), pale yellow powder, mp>240° C.

I.R. $\nu_{max}^{Nujol}$: 3330, 3200, 3100, 1770, 1690 cm$^{-1}$

N.M.R. $\delta$(D$_2$O; ppm): 3.42–3.61 (2H, m), 5.03–5.16 (1H, m), 5.19 (1H, s), 5.60 (1/2H, d, J=5 Hz), 5.79 (1/2H, d, J=5 Hz), 6.36–6.50 (1H, m), 8.32 (1H, s)

EXAMPLE 7

To a stirred solution of 7-[2-(2-amino-4-thiazolyl)glyoxyloylamino]-3-cephem-4-carboxylic acid (520 mg) in methanol (15 ml) was added sodium borohydride (100 mg) under ice-cooling, and stirred at the same temperature for 3 hours. Methanol was distilled off under reduced pressure from the reaction mixture, and the residue was dissolved in water (3 ml) and adjusted to pH 3 with 6 N-hydrochloric acid. The precipitates were collected by filtration, washed with water and dried over phosphorus pentoxide to give 7-[2-(2-amino-4-thiazolyl)-2-hydroxyacetamido]-3-cephem-4-carboxylic acid (290 mg).

I.R. $\nu_{max}^{Nujol}$: 1775, 1630 cm$^{-1}$

N.M.R. $\delta$(D$_2$O+DMSO-d$_6$, ppm): 5.03 (1H, s), 5.07 (1H, d, J=4.6 Hz), 5.72 (1H, d, J=4.6 Hz), 6.49 (1H, m, J=3.2 Hz), 6.67 (1H, s)

EXAMPLE 8

A solution of 7-[2-(2-amino-4-thiazolyl)glyoxyloylamino]-3-cephem-4-carboxylic acid hydrochloride (1.78 g) in water (100 ml) was adjusted to pH 6.0 with sodium bicarbonate under ice-cooling with stirring. Sodium acetate (0.38 g) and methoxylamine hydrochloride (1.37 g) were added to the solution adjusted to pH 7.0 with sodium bicarbonate and then stirred at 48° C. for an hour. The resultant solution was washed with ethyl acetate (200 ml) and diethyl ether (100 ml) in turn, and then nitrogen gas was bubbled into the solution to remove diethyl ether. The aqueous solution was adjusted to pH 3.5 with 10% hydrochloric acid under ice-cooling with stirring. The precipitates were collected by filtration, washed with water and dried over phosphorus pentoxide under reduced pressure to give 7-[2-(2-amino-4-thiazolyl)-2-methoxyiminoacetamido]-3-cephem-4-carboxylic acid (syn isomer, 120 mg). The mother liquor was subjected to column chromatography on macroporous, nonionic adsorption resin "Diaion HP-20" (Trademark: manufactured by Mitsubishi Chemical Industries Ltd.) and eluted with 40% aqueous acetone. The eluate was concentrated under reduced pressure, lyophilized, and then dried over phosphorus pentoxide to give the same object compound (950 mg). Total yield 1070 mg.

I.R. $\nu_{max}^{Nujol}$: 3460, 3290, 3150, 1780, 1655 1623 cm$^{-1}$

N.M.R. $\delta$(DMSO-d$_6$, ppm): 3.60 (2H, broad s), 3.84 (3H, s), 5.12 (1H, d, J=5 Hz), 5.84 (1H,d,d, J=5 Hz, 8 Hz), 6.52 (1H, t), 6.76 (1H, s), 7.26 (2H, broad s), 9.65 (1H, d, J=8 Hz)

EXAMPLE 9

The following compounds may be prepared in a similar manner to that of Example 8.

(1) 7-[2-(2-aminothiazol-4-yl)-2-hydroxyiminoacetamido]-3-cephem-4-carboxylic acid (syn isomer)

I.R. $\nu_{max}^{Nujol}$: 3350-3200, 1770, 1670, 1630 cm$^{-1}$

N.M.R. $\delta$(DMSO-d$_6$, ppm): 3.60 (2H, broad s), 5.10 (1H, d, J=5 Hz), 5.83 (1H, dd, J=5 Hz, 8 Hz), 6.47 (1H, t, J=4 Hz), 6.67 (1H, s), 9.47 (1H, d, J=8 Hz)

(2) 7-[2-(2-aminothiazol-4-yl)-2-ethoxyiminoacetamido]-3-cephem-4-carboxylic acid (syn isomer)

I.R. $\nu_{max}^{Nujol}$: 3500, 3300, 3200, 1785, 1625, 1600 cm$^{-1}$

N.M.R. δ(DMSO-d$_6$, ppm): 1.20 (3H, t, J=7 Hz), 3.57 (2H, m), 4.08 (2H, q, J=7 Hz), 5.08 (1H, d, J=5 Hz), 5.83 (1H, dd, J=5 Hz, 8 Hz), 6.47 (1H, m), 6.73 (1H, s), 7.20 (2H, m), 9.58 (1H, d, J=8 Hz)

(3) 7-[2-(2-aminothiazol-4-yl)-2-propoxyiminoacetamido]-3-cephem-4-carboxylic acid (syn isomer)

I.R. $\nu_{max}^{Nujol}$: 3250, 1770, 1650, 1660, 1620 cm$^{-1}$

N.M.R. δ(DMSO-d$_6$, ppm): 0.93 (3H, t, J=7 Hz), 1.67 (2H, sextet, J=7 Hz), 3.60 (2H, m), 4.03 (2H, t, J=7 Hz), 5.13 (1H, d, J=5 Hz), 5.83 (1H, dd, J=5 Hz, 8 Hz), 6.48 (2H, t, J=4 Hz), 6.70 (1H, s), 7.18 (2H, m), 9.53 (1H, d, J=8 Hz)

(4) 7-[2-(2-aminothiazol-4-yl)-2-butoxyiminoacetamido]-3-cephem-4-carboxylic acid (syn isomer)

I.R. $\nu_{max}^{Nujol}$: 3320, 1775, 1660 cm$^{-1}$

N.M.R. δ(DMSO-d$_6$, ppm): 0.88 (3H, t, J=7 Hz), 1.1–1.9 (4H, m), 3.58 (2H, broad, s), 4.05 (2H, t, J=7 Hz), 5.08 (1H, d, J=5 Hz), 5.80 (1H, dd, J=5 Hz, 8 Hz), 6.44 (1H, broad s), 7.18 (2H, s), 9.51 (1H, d, J=8 Hz)

(5) 7-[2-(2-aminothiazol-4-yl)-2-pentyloxyiminoacetamido]-3-cephem-4-carboxylic acid (syn isomer).

I.R. $\nu_{max}^{Nujol}$: 3300, 1775, 1650, 1540 cm$^{-1}$

N.M.R. δ(DMSO-d$_6$, ppm): 0.6–2.0 (9H, m), 3.56 (2H, d, J=2 Hz), 4.03 (2H, t, J=6 Hz), 5.08 (1H, d, J=5 Hz), 5.81 (1H, dd, J=5 Hz, 8 Hz), 6.46 (1H, t, J=4 Hz), 6.69 (1H, s), 7.20 (2H, s), 9.15 (1H, d, J=8 Hz)

(6) 7-[2-(2-aminoathiazol-4-yl)-2-hexyloxyiminoacetamido]-3-cephem-4-carboxylic acid (syn isomer).

I.R. $\nu_{max}^{Nujol}$: 3250, 1760, 1640, 1600 cm$^{-1}$

N.M.R. δ(DMSO-d$_6$, ppm): 1.88 (3H, m), 1.1–1.9 (8H, m), 3.60 (2H, m), 4.06 (2H, t, J=6 Hz), 5.10 (1H, t, J=5 Hz), 5.82 (1H, dd, J=5 Hz, 8 Hz), 6.46 (1H, m), 6.70 (1H, s), 7.26 (2H, m), 9.56 (1H, d, J=8 Hz)

(7) 7-[2-(2-aminothiazol-4-yl)-2-allyloxyiminoacetamido]-3-cephem-4-carboxylic acid (syn isomer).

I.R. $\nu_{max}^{Nujol}$: 3300, 1780, 1660, 1630 cm$^{-1}$

N.M.R. δ(DMSO-d$_6$, ppm): 3.67 (2H, d, J=4 Hz), 4.67 (2H, m), 5.17 (1H, d, J=5 Hz), 5.25 (1H, m), 5.50 (1H, m), 5.90 (1H, dd, J=5 Hz, 8 Hz), 6.03 (1H, m), 6.55 (1H, m), 6.80 (1H, s), 7.50 (2H, m), 9.68 (1H, d, J=8 Hz)

(8) 7-[2-(2-aminothiazol-4-yl)-2-propargyloxyiminoacetamido]-3-cephem-4-carboxylic acid (syn isomer).

I.R. $\nu_{max}^{Nujol}$: 3500, 3300, 1780, 1720, 1660, 1630 cm$^{-1}$

N.M.R. δ(DMSO-d$_6$, ppm): 3.48 (1H, m), 3.67 (2H, m), 4.80 (2H, d, J=2 Hz), 5.17 (1H, d, J=5 Hz), 5.88 (1H, dd, J=5 Hz, 8 Hz), 6.55 (1H, m), 6.85 (1H, s), 7.33 (2H, m), 9.73 (1H, d, J=8 Hz)

(9) 7-[2-(2-aminothiazol-4-yl)-2-cyclohexyloxyiminoacetamido]-3-cephem-4-carboxylic acid (syn isomer)

I.R. $\nu_{max}^{Nujol}$: 3350, 1775, 1665, 1620, 1540 cm$^{-1}$

N.M.R. δ(DMSO-d$_6$, ppm): 0.8–2.2 (10H, m), 3.60 (2H, broad s), 4.04 (1H, m), 5.09 (1H, d, J=5 Hz), 5.83 (1H, dd, J=5 Hz, 9 Hz), 6.45 (1H, t, J=4 Hz), 6.67 (1H, s), 7.19 (2H, s), 9.48 (1H, d, J=9 Hz)

What we claim is:
1. A compound of the formula:

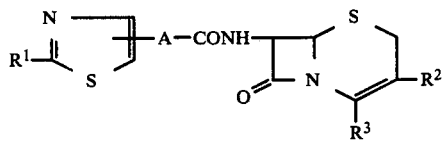

wherein
R$^1$ is amino or protected amino,
A is lower alkylene which may be substituted with oxo, hydroxy, amino, protected hydroxy or protected amino,
R$^2$ is hydrogen, and
R$^3$ is carboxy or functionally modified carboxy, and its nontoxic, pharmaceutically acceptable salt.

2. A compound according to claim 1, wherein A is lower alkylene.

3. A compound according to claim 2, which is 7-[2-(2-aminothiazol-4-yl)acetamido]-3-cephem-4-carboxylic acid and its 4-nitrobenzyl ester.

4. A compound according to claim 1, wherein A is oxo(lower)alkylene.

5. A compound according to claim 4, which is 7-[2-(2-aminothiazol-4-yl)glyoxyloylamino]-3-cephem-4-carboxylic acid.

6. A compound according to claim 4, which is 7-[2-(2-formamidothiazol-4-yl)glyoxyloylamino]-3-cephem-4-carboxylic acid and its 4-nitrobenzyl ester.

7. A compound according to claim 1, wherein A is hydroxy(lower)alkylene.

8. A compound according to claim 7, which is 7-[2-(2-aminothiazol-4-yl)-2-hydroxyacetamido]-3-cephem-4-carboxylic acid.

9. A compound according to claim 1, wherein A is amino(lower)alkylene.

10. A compound according to claim 9, which is 7-[2-(2-aminothiazol-4-yl)glycinamido]-3-cephem-4-carboxylic acid and its formate.

11. An antimicrobial pharmaceutical composition comprising, as an effective ingredient, the compound of the claim 1, in association with a pharmaceutically acceptable, substantially nontoxic carrier or excipient.

12. A method for treating an infectious disease caused by pathogens, which comprises administering the compound of claim 1 to infected human being or animals.

13. A compound of the formula:

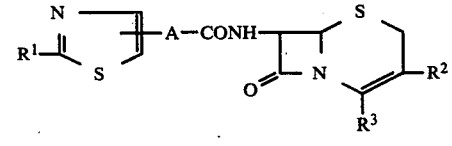

wherein
R$^1$ is amino or protected amino,
A is lower alkylene substituted with oxo,
R$^2$ is hydrogen, and
R$^3$ is carboxy or functionally modified carboxy, and its nontoxic, pharmaceutically acceptable salt.

* * * * *